(12) United States Patent
Mirov et al.

(10) Patent No.: US 10,656,009 B2
(45) Date of Patent: May 19, 2020

(54) CONTEXT DISCRIMINATION USING AMBIENT LIGHT SIGNAL

(71) Applicant: Verily Life Sciences LLC, Mountain View, CA (US)

(72) Inventors: Russell Norman Mirov, Los Altos, CA (US); Mark Murphy, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 224 days.

(21) Appl. No.: 14/332,594

(22) Filed: Jul. 16, 2014

(65) Prior Publication Data

US 2016/0018257 A1  Jan. 21, 2016

(51) Int. Cl.
*A61B 5/024* (2006.01)
*A61B 5/00* (2006.01)
(Continued)

(52) U.S. Cl.
CPC ........ *G01J 1/4204* (2013.01); *A61B 5/02416* (2013.01); *A61B 5/02438* (2013.01); *A61B 5/14551* (2013.01); *A61B 5/681* (2013.01); *A61B 5/6824* (2013.01); *G01J 1/0219* (2013.01); *G01J 1/0233* (2013.01);
(Continued)

(58) Field of Classification Search
CPC ........ A61B 5/02427; A61B 2560/0242; A61B 5/6823; A61B 5/055; A61B 5/0533; A61B 5/021; A61B 5/01; A61B 5/6828; A61B 5/6824; A61B 5/681; A61B 5/14551; A61B 5/02438; A61B 5/02416; G01J 1/4204; G01J 1/0233; G01J 1/0219; G09G 2360/144; G09G 2320/0646
See application file for complete search history.

(56) References Cited

U.S. PATENT DOCUMENTS 4,773,422 A * 9/1988 Isaacson ............ A61B 5/14551
                                                     600/326
5,874,731 A * 2/1999 Swanson ................ G01R 11/02
                                                      250/214 B
(Continued)

FOREIGN PATENT DOCUMENTS

WO    2013148753 A1    10/2013
WO    2014097020 A2     6/2014

OTHER PUBLICATIONS

International Search Report from International Application No. PCT/US2015/040604, dated Nov. 30, 2015.

*Primary Examiner* — Angela M Hoffa
*Assistant Examiner* — Aminah Asghar
(74) *Attorney, Agent, or Firm* — McDonnell Boehnen Hulbert & Berghoff LLP

(57) ABSTRACT

A system is configured to discriminate amongst different environments based in part on characteristics of ambient light. Ambient light intensity is measured using a light-sensitive element configured to generate an output signal indicative of an intensity of light incident on the light-sensitive element. A controller is configured to obtain a set of ambient light measurements using the light-sensitive element, and determine that the measurements correspond to a particular ambient light profile. The particular ambient light profile can be one of multiple ambient light profiles that each correspond to a different environment and/or context.

27 Claims, 7 Drawing Sheets

(51) Int. Cl.
*A61B 5/1455* (2006.01)
*G01J 1/42* (2006.01)
*G01J 1/02* (2006.01)
A61B 5/021 (2006.01)
A61B 5/055 (2006.01)
A61B 5/01 (2006.01)
A61B 5/053 (2006.01)

(52) U.S. Cl.
CPC ............... *A61B 5/01* (2013.01); *A61B 5/021* (2013.01); *A61B 5/055* (2013.01); *A61B 5/0533* (2013.01); *A61B 5/6823* (2013.01); *A61B 5/6828* (2013.01); *A61B 2560/0242* (2013.01)

(56) References Cited

U.S. PATENT DOCUMENTS

| | | | |
|---|---|---|---|
| 6,363,269 B1* | 3/2002 | Hanna | A61B 5/14551 600/322 |
| 6,616,613 B1 | 9/2003 | Goodman | |
| 8,571,620 B2 | 10/2013 | Cinbis et al. | |
| 8,909,312 B2* | 12/2014 | Sagan | A61B 5/14551 600/310 |
| 2004/0017300 A1* | 1/2004 | Kotzin | G08B 21/0453 340/870.11 |
| 2008/0055228 A1* | 3/2008 | Glen | G09G 3/3406 345/102 |
| 2008/0294016 A1* | 11/2008 | Gobeyn | A61B 5/103 600/301 |
| 2008/0294017 A1* | 11/2008 | Gobeyn | A61B 3/113 600/301 |
| 2010/0292593 A1* | 11/2010 | Tobola | A61B 5/02416 600/508 |
| 2011/0066381 A1* | 3/2011 | Garudadri | A61B 5/0002 702/19 |
| 2012/0001841 A1* | 1/2012 | Gokingco | G01J 1/32 345/102 |
| 2012/0019492 A1* | 1/2012 | Barnhoefer | H05B 33/0851 345/207 |
| 2012/0232354 A1* | 9/2012 | Ecker | A61B 5/046 600/300 |
| 2012/0256080 A9* | 10/2012 | Mikat | B60J 3/04 250/214 R |
| 2012/0271121 A1 | 10/2012 | Della Torre et al. | |
| 2013/0078976 A1* | 3/2013 | Naftolin | H04M 1/72569 455/418 |
| 2013/0109949 A1* | 5/2013 | Li | G01N 21/1702 600/407 |
| 2013/0197327 A1* | 8/2013 | Chen | A61B 5/14556 600/317 |
| 2013/0248691 A1 | 9/2013 | Mirov et al. | |
| 2014/0021869 A1* | 1/2014 | Kerr | G06F 1/1616 315/158 |
| 2014/0094663 A1 | 4/2014 | LeBoeuf et al. | |
| 2014/0132578 A1 | 5/2014 | Zheng | |
| 2014/0215246 A1* | 7/2014 | Lee | G06F 1/3206 713/323 |
| 2014/0243633 A1* | 8/2014 | Addison | A61B 5/14552 600/340 |
| 2016/0158572 A1* | 6/2016 | Nolan | A61N 5/0618 607/88 |

* cited by examiner

CONTEXT DISCRIMINATION USING AMBIENT LIGHT SIGNAL

BACKGROUND

Unless otherwise indicated herein, the materials described in this section are not prior art to the claims in this application and are not admitted to be prior art by inclusion in this section.

Artificial fluorescent or incandescent lighting is typically modulated by the mains frequency of the alternating current (AC) electrical power from the grid. Thus, in the US, lighting is typically modulated at 120 Hertz (due to 60 Hertz utility waveform reaching maximum voltage difference twice per cycle), and in Europe, lighting is typically modulated at 100 Hertz (due to the 50 Hertz utility waveform). Other light sources may be intensity modulated at other frequencies. For example, lighting on an aircraft is modulated by the 400 Hz AC power source used in aircraft. Light from a projection movie screen is modulated at about 24 Hz or 48 Hz, depending on the frame rate. Similarly, television and computer monitors emit light with a characteristic flicker that depends on the refresh rate of the display panel. Natural light environments (i.e., from the Sun) may thus be characterized by steady light—an absence of flicker modulation Optical pulse meters operate by detecting optical signatures of pulsing blood flow through body tissue. A typical optical pulse meter includes a light source and a light sensor that is positioned to detect light emitted by the light source that is either reflected from the body tissue or transmitted through the body tissue. The optical signals provide indications of pulsing blood flow due to periodic variations in the amount of reflected/transmitted light due to the time-variant amount of blood in the vasculature structure. The intensity of measured light depends on the amount of blood in the body tissue (e.g., vasculature structure) during a given measurement. Periodic variations in the intensity of measured light are due to pulsing of the blood. Thus, the pulse rate can be determined based on the intensity modulation frequency of a set of light sensor measurements. In addition, the oxygenation level of the arterial blood can be determined based on the strength of the reflected/transmitted light signal. Hemoglobin-containing blood is more transmissive to red light than to infrared light. Thus, one example may involve illuminating body tissue with both red light and infrared light and using the difference in the light reflected/transmitted at the two wavelengths to isolate effects from pulsing arterial blood as opposed to other body tissue and/or venous blood. For instance, by observing differences in the relative amount of light reflected and/or transmitted at multiple wavelengths, such as red and infrared light ranges, the time-variant amount of blood can be evaluated, and the oxygenation level and/or pulse rate can be determined.

SUMMARY

A system is configured to discriminate amongst different environments based in part on characteristics of ambient light. Ambient light intensity is measured using a light-sensitive element configured to generate an output signal indicative of an intensity of light incident on the light-sensitive element. A controller is configured to obtain a set of ambient light measurements using the light-sensitive element, and determine that the measurements correspond to a particular ambient light profile. The particular ambient light profile can be one of multiple ambient light profiles that each correspond to a different environments and/or contexts.

Some embodiments of the present disclosure provide a system including a light-sensitive element and a controller. The light-sensitive element can be configured to generate an output signal indicative of an intensity of light incident on the light-sensitive element. The controller can be configured to: (i) obtain a set of ambient light measurements using the light-sensitive element; (ii) determine that the obtained set of ambient light measurements corresponds to a particular one of multiple ambient light profiles; and (iii) in response to determining that the obtained set of ambient light measurements corresponds to the particular one of the multiple ambient light profiles, generate an indication that the obtained set of ambient light measurements corresponds to the particular one of the multiple ambient light profiles. The set of ambient light measurements can include data values indicative of ambient light intensities.

Some embodiments of the present disclosure provide a method. The method can include obtaining a set of ambient light measurements using a light-sensitive element configured to generate an output signal indicative of an intensity of light incident on the light-sensitive element. The set of ambient light measurements can include data values indicative of ambient light intensities. The method can also include determining that the obtained set of ambient light measurements corresponds to a particular one of multiple ambient light profiles. The method can also include generating an indication that the obtained set of ambient light measurements corresponds to the particular one of the multiple ambient light profiles in response to determining that the obtained set of ambient light measurements corresponds to a particular one of multiple ambient light profiles.

Some embodiments of the present disclosure provide a body-mountable device including a housing, a light-sensitive element, and a controller. The housing can include a body-mountable surface. The light-sensitive element can be mounted to the housing. The light-sensitive element can be configured to generate an output signal indicative of an intensity of incident light. The light-sensitive element can be situated such that, while the body-mountable surface is mounted over body tissue, at least a portion of light incident on the light-sensitive element passes through the body tissue. The controller can be configured to: (i) obtain a set of ambient light measurements using the light-sensitive element; (ii) determine that the obtained set of ambient light measurements corresponds to a particular one of multiple ambient light profiles; and (iii) in response to determining that the obtained set of ambient light measurements corresponds to the particular one of the multiple ambient light profiles, generate an indication that the obtained set of ambient light measurements corresponds to the particular one of the multiple ambient light profiles. The set of ambient light measurements can include data values indicative of ambient light intensities.

Some embodiments of the present disclosure provide means for obtaining a set of ambient light measurements using a light-sensitive element configured to generate an output signal indicative of an intensity of light incident on the light-sensitive element. Some embodiments of the present disclosure provide means for determining that the obtained set of ambient light measurements corresponds to a particular one of multiple ambient light profiles. Some embodiments of the present disclosure provide means for generating an indication that the obtained set of ambient light measurements corresponds to the particular one of the multiple ambient light profiles in response to determining that the obtained set of ambient light measurements corresponds to a particular one of multiple ambient light profiles.

These as well as other aspects, advantages, and alternatives, will become apparent to those of ordinary skill in the art by reading the following detailed description, with reference where appropriate to the accompanying drawings.

DETAILED DESCRIPTION

Figure 1A:
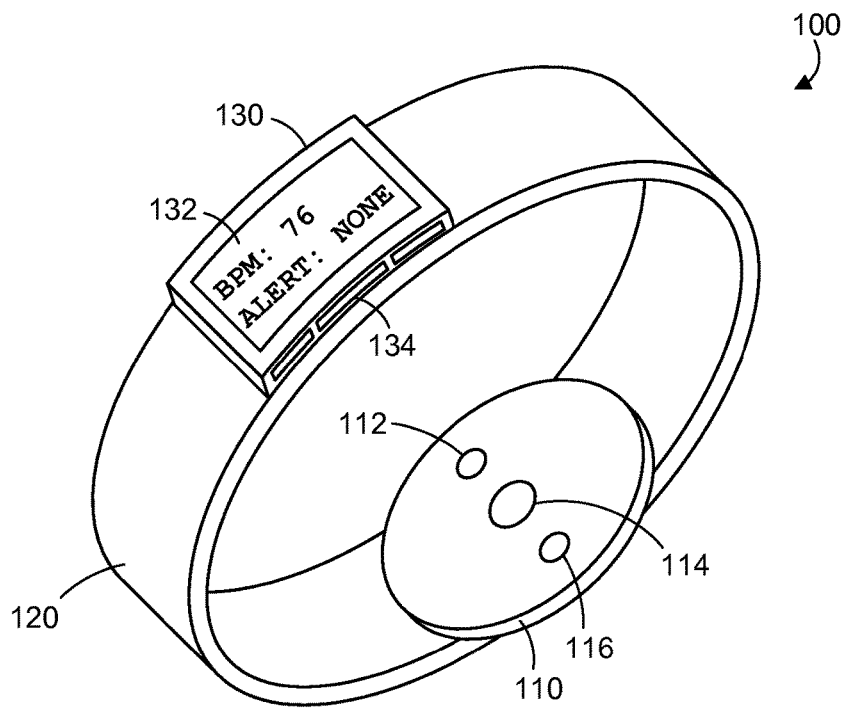
FIG. 1A shows an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A system is configured to discriminate amongst different environments based in part on characteristics of ambient light. Ambient light intensity is measured using a light-sensitive element configured to generate an output signal indicative of an intensity of light incident on the light-sensitive element. A controller is configured to obtain a set of ambient light measurements using the light-sensitive element, and determine that the measurements correspond to a particular ambient light profile. The particular ambient light profile can be one of multiple ambient light profiles that each correspond to a different environment and/or context.

The ambient light sensor may be mounted on a wearable device, and used to analyze an environmental context of the wearer of the device. For instance, a health-monitoring wearable device may include a variety of sensors, including one or more light sensors. Such a health-monitoring wearable device may be used to collect measurements related to health states of the wearer of the device. Such measurements may include, for example, indications of an analyte concentration, a pulse rate, a temperature, and other indicators useful for health monitoring and/or diagnosis. A wearable device may also include a light-sensitive element that can be used to obtain measurements of ambient light intensity. A set of ambient light measurements can then be analyzed and a determination can be made regarding which of multiple ambient light profiles the measurements correspond to.

For instance, the device may include an optical pulse oximetry system that measures light reflected or transmitted by body tissue and uses such measurements to determine characteristics of blood flow (e.g., arterial blood flow) in the tissue. The sensing system may include both a light source that emits light into the tissue and a light-sensitive element that detects the light that is transmitted or reflected by the tissue. To account for variations in ambient light, the sensing system may also obtain measurements of ambient light, such as by measuring light intensity while the light source is turned off. In addition to being used for calibration of the pulse oximetry system, such ambient light measurements can also be used to determine a corresponding ambient light profile, and thus an environmental context of the device.

A control system can analyze the measurements to characterize the environment in which the device is located. In practice, the analysis can include determining an extent of correspondence between the set of ambient light measurements and multiple ambient light profiles, and identifying a particular profile with the greatest extent of correspondence and/or which exceeds a threshold extent of correspondence. For example, the ambient light profiles may include information indicating an intensity modulation frequency and/or intensity modulation amplitude. Extents of correspondence may then be determined by determining intensity modulation frequencies and/or amplitudes for the set of ambient light measurements and computing values based on degrees of agreement between the profiles and the measured frequencies and/or amplitudes. For example, ambient intensity modulation of 120 Hz or 100 Hz may be associated with artificial light flicker due to 60 Hz or 50 Hz AC power. In another example, ambient intensity modulation of 800 Hz may be associated with artificial light flicker aboard an aerial vehicle that uses 400 Hz AC power. In another example, ambient intensity modulation may correspond to a refresh frequency of a computer monitor. In another example, stable (i.e., not flickering) ambient light may be associated with natural (solar) lighting. In still another example, ambient intensity modulation at about 24 Hz or 48 Hz that varies in intensity over time may be associated with a movie theater projection display or television display. Other examples of characteristic light profiles associated with various environments are also possible.

The control system can operate the ambient light sensor to periodically obtain measurements of the intensity of incident light. The ambient light sensor may include, for example, a photodiode, a photovoltaic cell, or another element configured to generate an electrical signal (e.g., a current or voltage) that relates to the intensity of incident light during a given integration period. Analog electrical signals generated by the ambient light sensor may be converted to digital values using an analog to digital converter and/or other signal conditioning components such as filters, amplifiers, trans impedance amplifiers, etc. The digital values from a series of such measurements can then be analyzed by a computing system to identify characteristics of the measured ambient light, such as intensity modulation frequency and/or amplitude. For example, the computing system may identify a periodic light flicker with a certain frequency. The computing system can then determine that the measurements correspond to one of multiple predetermined profiles, and responsively generate an indication that the ambient light measurements correspond to the determined one of the predetermined profiles.

The indication that the ambient light measurements correspond to one of the ambient light profiles may then be used, at least in part, to determine the environment and/or context of the wearable device, and by extension the wearer of the body-mountable device. Such environmental/contextual information can then be analyzed to identify behavioral patterns and/or metrics useful for a variety of purposes. For example, the information may be used in combination with other information to determine the length of time that the wearer spends outside versus indoors (in the presence of artificial light), or may be used to determine the length of time the wearer is in the presence of a computer monitor and/or television. Moreover, the environmental/contextual indication may be used as a basis to modify a user interface setting of the wearable device or another device communicatively linked with the wearable device. For instance, upon determining a wearer is in a cinema, the wearer's cell phone may be automatically set to vibrate. Or, upon determining the wearer is aboard an aircraft, the wearer's wireless communication device(s) may be set to airplane mode. Other examples are also possible.

II. Example Wearable Device

FIG. 1A shows an example wearable device 100. The wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In some examples, the wearable device(s) described herein may be configured to be removably mounted to a body surface and may include body-mounting surfaces. In order to take in vivo measurements in a non-invasive manner from outside of the body, the wearable device 100 may be positioned on a portion of the body where subsurface vasculature or other elements of the body of the wearer may be detected, which depends in part on the type of detection system used and its sensitivity. The wearable device 100 may be placed in close proximity to the skin or tissue. Depending on the mounting location of the device 100, the device may accordingly be implemented in a variety of different form factors that are configured to be mounted to a variety of different body surfaces. One such example is a wrist-mountable device that is shown in FIG. 1A. As shown in FIG. 1A, the example wrist-mounted device 100 includes a sensor housing 110, a mounting band 120, a user interface module 130.

A. Sensor(s)

Figure 1B:
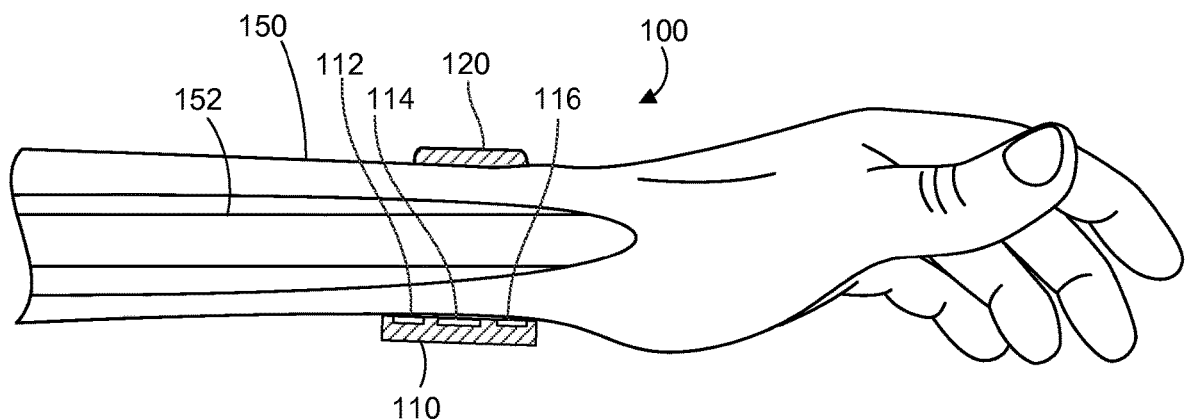
FIG. 1B is a side cross-sectional view of the example wearable device shown in FIG. 1A when worn on a wrist.

The sensor housing 110 is disposed on the mount 120 to facilitate contact between the body surface and the sensor housing 110 when the device 100 is worn. For instance, FIG. 1B shows the example device 100 in a side cross-sectional view when the device 100 is mounted to a wrist. As shown in FIG. 1B, the sensor housing 110 is situated over the body surface (e.g., the anterior side, or palmar side, of the wrist above the ulnar artery). The sensor housing 110 may include at least one sensor for detecting at least one physiological property of the body of the wearer, which could include any parameters that may relate to the health of the person wearing the wearable device. For example, the sensor housing 110 includes a pulse rate sensor and/or pulse oximetry sensor having two light-sensitive elements 112, 116, and a light emitter 114. While the device 100 is mounted over a wrist (as in FIG. 1B), the light emitter 114 can emit light into the body tissue. Some of the emitted light is then reflected by the tissue and received by the light-sensitive elements 112, 116. The tissue of the arm 150 includes a variety of materials with different degrees of reflectivity, such as skin, muscle, bone, connective tissues, vasculature 152, etc., and so the intensity of reflected light during a given measurement depends on the composition of the tissue over the sensor. Over timescales of a few seconds the tissue composition remains fairly constant with the exception of arterial blood that traverses the vasculature 152 in a non-continuous, pulsing manner related to the wearer's heartbeat. Intensity modulations in the reflected light can be attributed to the pulsing arterial blood in the vasculature 152 (e.g., through the ulnar artery), and so the frequency of such intensity modulations can be used to determine the wearer's pulse rate.

Other sensors may additionally or alternatively be included in the sensor housing 110. The sensor housing 110 could be configured to with sensors for measuring blood pressure, galvanic skin response, skin temperature, analyte levels, etc. In a non-exhaustive list, the sensor housing 110 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. Additionally, sensors and other components disposed in or within the housing 110 may be miniaturized so that the wearable device 100 may be worn on the body without significantly interfering with the wearer's activities and/or use of her arm.

B. Power System

The wearable device 100 additionally includes a power system for operating the electronics components therein. The power system may include a conductive coil (not shown) for receiving electromagnetic energy from a wireless charging system. The coil could be enclosed within the sensor housing 110 proximate the boundary of the sensor housing 110 such that the coil could efficiently receive electromagnetic energy emitted by a wireless charger (not shown) when the wearable device 100 is disposed on such a wireless charger. The wearable device 100 can additionally include a rechargeable battery (not shown) configured to power electronics within the wearable device 100. A recharger (not shown) of the wearable device 100 is configured to recharge the rechargeable battery using electromagnetic energy received using the coil. For instance, the recharger may rectify and/or regulate voltage fluctuations across the coil caused by the wireless charger, and use the rectified voltage to charge the rechargeable battery.

C. Mount

The mounting band 120 can be used to mount the device 100 at, on or in proximity to the body surface. The mount 120 may prevent the wearable device 100 from moving relative to the body to reduce measurement error and noise. In one example, as shown in FIG. 1A, the mount 120 may take the form of a strap or band that can be worn around a part of the body, such as a wrist, ankle, arm, leg, waist, and/or chest. In some examples, the device 100 may additionally or alternatively include an adhesive substrate for mounting the wearable device 100 to a body surface.

D. User Interface

The wearable device 100 may also include a user interface 130 via which the wearer of the device may receive outputs and provide inputs to the device 100. Outputs may include, for example, recommendations or alerts based on physiological measurements obtained using the wearable device and/or other information related to the device, such as battery condition or status information. Inputs may include adjustments to settings on the device (e.g., measurement interval, data reporting format, etc.). As shown in FIG. 1A, the user interface 130 can include a display 132 for providing outputs, and buttons 134 for receiving user inputs. As shown in FIG. 1A, the display can include text that indicates a heart rate of 76 beats per minute and no alerts (e.g., "BPM: 76 ALERTS: NONE"). Although the user interface 130 may include a variety of other components to provide and/or receive information via visual component(s) (e.g., a display and/or a camera), auditory component(s) (e.g., an audio loudspeaker and/or a microphone), and/or tactile component(s) (e.g., a vibration generator and/or an accelerometer).

In some examples, the user interface 130 may additionally or alternatively be implemented via communication between the wearable device 100 and other device(s). For instance, a wearer may receive outputs (e.g., alerts) via their cell phone, computer, or other device. The wearer may also provide inputs (e.g., to adjust settings of the device) via such other device. Accordingly, the wearable device 100 can be configured to communicate with such other devices via wireless signals, for example. In addition, the wearable device 100 may communicate with other devices, which may be used to store and/or process data related to the physiological measurements alone or in coordination with the processing performed locally by the device 100. For instance, a communicatively coupled computing system may receive data indicating a set of ambient light measurements from the wearable device 100, analyze the measurements, and determine corresponding environments/contexts. Such a computing system may also store indications of the wearer's contexts over time, and provide reports on the same (e.g., cumulative time spent near a computer monitor in a given day or week).

E. Example Wrist-Mounted Device

Figure 2A:
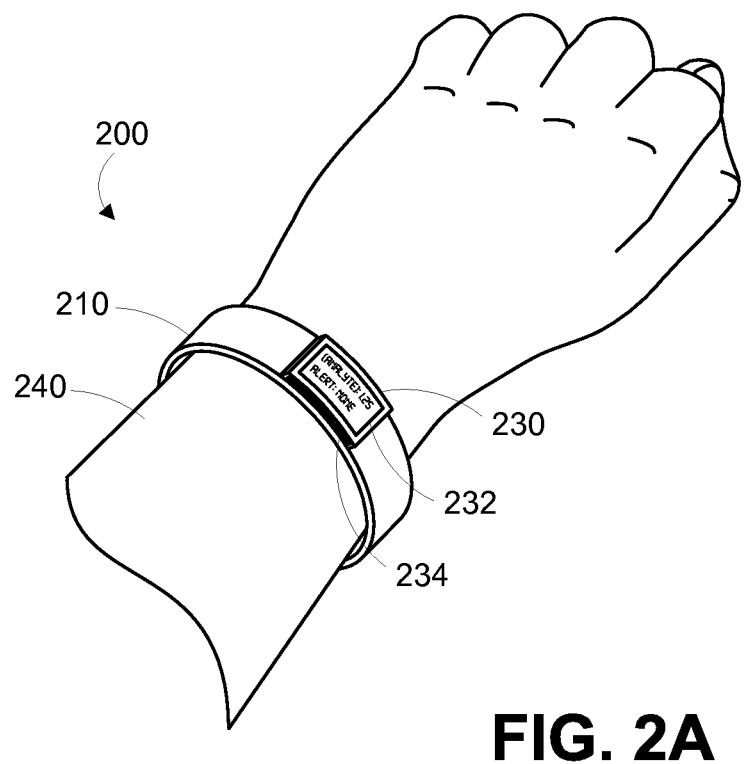
FIG. 2A is a top view of an example device worn on a wrist.
Figure 2B:
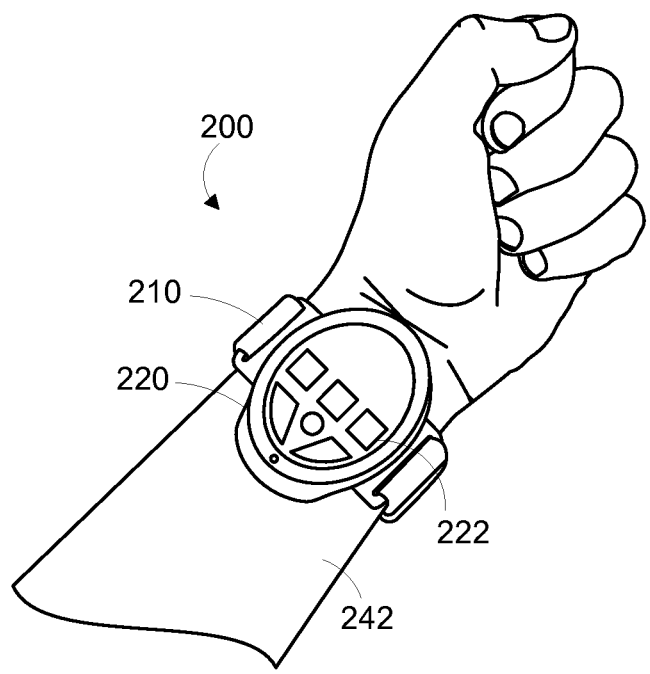
FIG. 2B is a reverse view of the example device shown in FIG. 2A when worn on a wrist.

FIG. 2A is a top view of an example wrist-mounted device 200 worn on a wrist. FIG. 2B is a reverse view of the example wrist-mounted device 200 shown in FIG. 2A. The wrist-mounted device 200 may be mounted to the wrist, similar to a watch or bracelet. FIGS. 2A and 2B show opposing views of the wrist-mounted device 200 being worn on the wrist. FIG. 2A shows a perspective in which a posterior side 240 of the wrist is visible; FIG. 2B shows a perspective in which an anterior side 242 of the wrist is visible.

The wrist mounted device 200 can include a wristband 210, a sensor housing 220, and a user interface 230. As shown in FIGS. 2A and 2B, when the device 200 is mounted to the wrist, the sensor housing 220 can be positioned over the anterior side 242 of the wearer's wrist, and the user interface 230 can be positioned on the posterior side 240 of the wearer's wrist. The wearer of the device 200 may receive, via the user interface 230, one or more recommendations or alerts related to physiological measurements obtained using the wrist-mounted device 200. Such a configuration may be perceived as natural for the wearer of the device 200 in that it is common for the posterior side 240 of the wrist to be observed, such as during the act of checking a wrist-watch. Accordingly, the wearer may easily view a display 232 of the user interface 230. Further, the sensor housing 220 may be located on the anterior side 242 of the wearer's wrist where the subsurface vasculature or other elements of the wearer's body (e.g., carpal tunnel, ulnar artery, etc.) may be readily observable via the physiological sensors within the sensor housing 220. However, other implementations may have other configurations.

The display 233 may be configured to display a visual indication of an alert, recommendation, and/or an indication of the measured physiological parameters, for instance, the presence or concentrations of certain blood analytes being measured, a pulse rate, an oximetry measurement, etc. Further, the user interface 230 may include one or more buttons 234 for accepting inputs from the wearer. Additionally or alternatively, the sensor housing 220 may also include one or more buttons 222 for accepting inputs from the wearer. The user inputs may be used to adjust settings of the wearable device 200, such as user interface settings (e.g., the manner of displaying information on the display 234), aspects of the data collection system (e.g., measurement intervals, initiation of measurement, communication settings, other aspects related to the functioning of the device 200, and/or or indications of the wearer's current health state (i.e., normal, migraine, shortness of breath, heart attack, fever, "flu-like" symptoms, food poisoning, etc.).

III. Optical Blood Flow Sensor

Figure 3A:
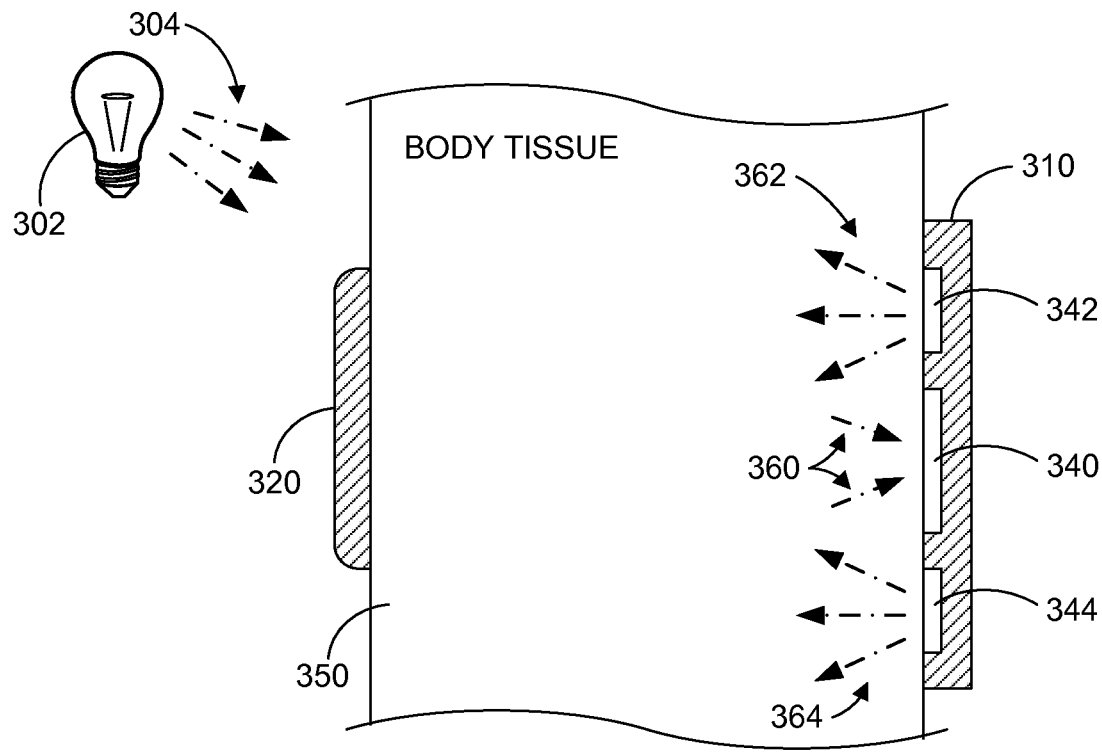
FIG. 3A is a simplified cross-sectional view of an example body-mountable device that measures light reflected or transmitted through tissue to sense blood flow.

FIG. 3A is a cross-sectional view of a wearable device for measuring properties of blood flow based on light that is reflected and/or transmitted by body tissue 350. For instance, the wearable device may detect a wearer's pulse rate. The wearable device can include a sensor housing 310 and a mount 320 that secures the sensor housing 310 against the body tissue 350 (e.g., against a skin surface). For example, the mount 320 may be a wristband that can secure the sensor housing against a wearer's wrist. The sensor housing 310 can include a light sensor 340 and light sources 342, 344 mounted along a tissue-facing surface of the sensor housing 310. The light sensor 340 can be a photodiode, or another light-sensitive device, and can have a light-receiving area arranged to receive light from the body tissue 350. The light sources 342, 344 may be light emissive diodes or other emissive devices and can be arranged to emit light directed into the body tissue 350. For example, when the wearable device is mounted against body tissue, the light-emissive areas of the light sources 342, 344 and the light-sensitive area of the light sensor 340 can be disposed along skin of the body tissue 350.

The light sensor 340 and light sources 342, 344 may optionally be mounted on a flexible printed circuit board (PCB). Such a flexible PCB may be used to facilitate conformance of the light sensor 340 and light sources 342, 344 with the skin surface of the body tissue 350. Other components of the sensor housing (e.g., amplifiers, filters, processors, communications modules, etc.) may be mounted on one or more locations and connected to the components on the flexible PCB through traces on the flexible PCB. In some examples, the sensor housing 310 may additionally or alternatively include one or more other sensors and/or user interface components, such as the sensor(s) and user interface components described above in connection with FIGS. 1-2.

In practice, the light sources 342, 344 can emit light 362, 364 toward the body tissue 350. The emitted light is transmitted through and/or reflected by various features within the body tissue 350 (e.g., skin, muscle, bone, vasculature, connective tissues, etc.). The emitted light 362, 364 may be at least partially reflected by the body tissue 350. The light sensor 340 can receive at least some of the light that is reflected by the body tissue 350. Thus, the intensity of detected light 360 may depend, at least in part, on the composition of the body tissue 350 in the vicinity of the sensor housing 310 (e.g., near enough to influence the detected light 360 via transmission and/or reflection). In addition, the light sensor 340 also receives some light that is transmitted and/or reflected through the body tissue 350 from external sources, such as ambient light 304 from an artificial light source 302. The intensity of the detected light 360 may therefore depend at least partially on the intensity of the emitted light 362, 364, the intensity of the ambient light 304, and the tendency of the body tissue 350 to transmit and/or reflect the light to allow it to be received by the light sensor 340.

Because arterial blood pulses through the vasculature structures within the body tissue 350, the amount and/or concentration of arterial blood influencing the detected light 360 reaching the light sensor 340 during a given measurement integration time is not constant. Instead, the amount of arterial blood may vary depending on the phase of the cardiac pulse cycle during a given measurement. The pulsing of the arterial blood may therefore be determined from a frequency of intensity modulations of a set of measurements. Moreover, a variety of other properties of the wearer's blood and/or vasculature may be determined based on a set of light intensity measurements. For instance, the amount of reflected light and/or the differential reflectivity of light at different wavelengths may be measured to provide indications of blood oxygenation (e.g., hemoglobin concentration), such as in blood oximetry. Further, the two light sources 342, 344 may each emit light with a different wavelength (e.g., visible light and infrared light) to obtain measurements relating to the differential reflection/transmission of the body tissue 350 at different wavelengths.

Figure 3B:
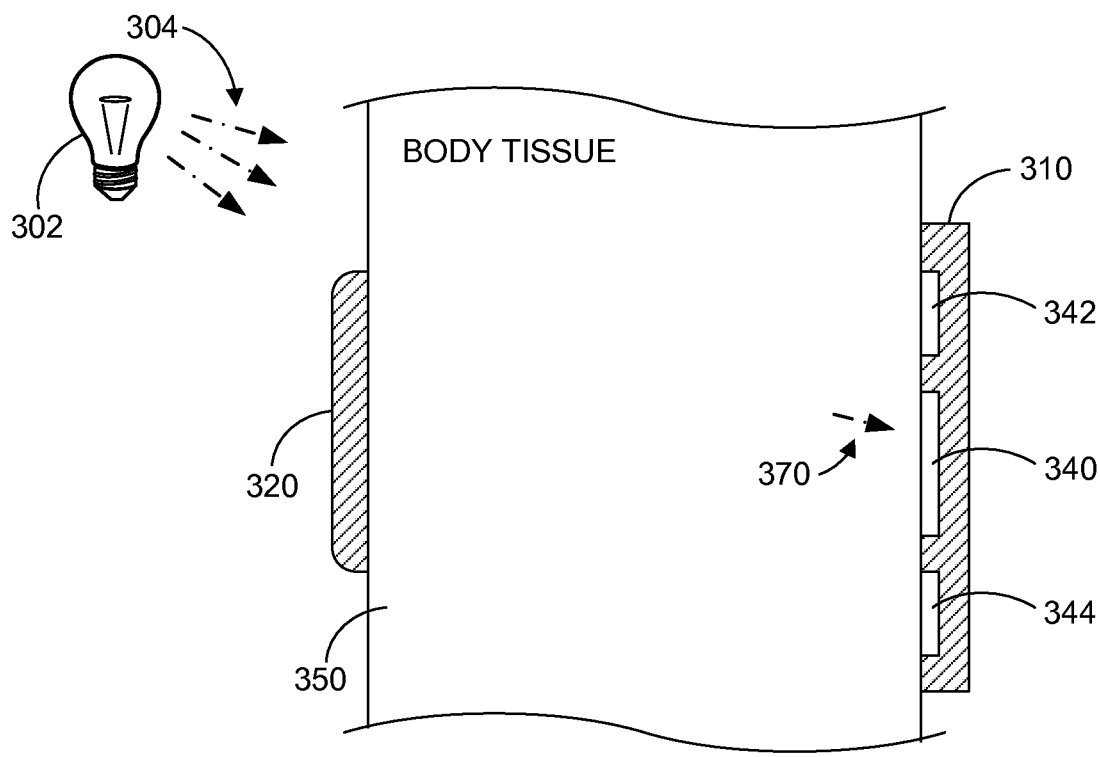
FIG. 3B is a simplified cross-sectional view of the example body-mountable device shown in FIG. 3A when measuring ambient light intensity.

To accurately identify the modulation due to differential reflection and/or transmission of the pulsing arterial blood within the vasculature structure, it is desirable to account for variations in ambient lighting conditions. FIG. 3B is a cross-sectional view of the wearable device shown in FIG. 3A when measuring ambient light intensity. During the ambient light measurement integration time, the light sources 342, 344 can be turned off, and the light sensor 340 can detect incident light 370. The incident light 370 can be light that is transmitted and/or reflected through the body tissue 350, such as the ambient light 304 from the artificial light source 302. The intensity of the ambient light (e.g., FIG. 3B) can be compared with the intensity of the detected light (e.g., FIG. 3A) to determine the contribution of the detected light 360 due to ambient light 304. For example, once the ambient light is determined, the ambient light may be subtracted from the light measurements obtained while the light sources 342, 344 are turned on to thereby account for ambient lighting conditions.

In some examples, the disclosed wearable device may be configured to alternate between oximetry/pulse measurements (e.g., as in FIG. 3A) and ambient light measurements (e.g., as in FIG. 3B). By alternating measurements, variations in ambient light levels can be accounted for on a measurement-by-measurement basis, for example. In some cases, the wearable device may obtain samples at about 100 Hz to about 200 Hz.

Moreover, the ambient light 304 itself may not be constant. For instance, artificial light sources such as incandescent and fluorescent light sources emit light that is modulated due to the AC power supply that powers such light sources with an AC voltage waveform. In an incandescent light source, a filament emits light in response to a voltage applied across the emissive element that heats the filament and causes it to radiate. The intensity of emitted light increases at higher voltages. An incandescent light source powered by an AC voltage supply therefore reaches maximum voltage twice per cycle of the waveform (the applied voltage peaks at each maxima and minima of the AC waveform). Similarly, the light source has two minima per cycle of the AC waveform (e.g., at each zero crossing of the AC waveform), although the filament may continue to emit light through the minima as well due to the heat capacity of the filament. Similarly, a fluorescent light source applies an AC voltage across electrodes in a fluorescent chamber to energize particles therein and thereby cause energy transitions that emit visible light. Therefore, an artificial light source powered by a 60 Hz AC supply emits light that is intensity modulated at 120 Hz.

Other examples of characteristic ambient lighting characteristics are also possible in other environments. For instance, an artificial light source powered by a 50 Hz AC supply emits light that is intensity modulated at 100 Hz; and an artificial light source powered by a 400 Hz AC supply (e.g., aboard an aircraft) emits light that is intensity modulated at 800 Hz. Moreover, some environments have ambient light that is intensity modulated with characteristic variations in frequency and/or amplitude. In another example, a television display or projection movie theater display may emit light that is intensity modulated at the frame rate or refresh rate of the display (e.g., about 24 Hz or about 48 Hz). While the frequency of intensity modulation in such environments may be stable, the amplitude may vary over time (e.g., between dark scenes and light scenes in a movie). In another example, ambient light from a computer display may be intensity modulated at a refresh rate of the display, but have relatively low variations in amplitude over time. For example, computer displays may be used to display a user interface with substantially static content (e.g., a word processing interface, a command/control interface, an email communication system). In yet another example, natural lighting (e.g., solar lighting) may be characterized by an absence of intensity modulations.

While the blood flow sensor is described by way of example in an implementation in which the sensor housing 310 includes one light sensor 340 and two light sources 342, 344, which may emit light at different wavelengths, other examples are possible. In some implementations, a blood flow sensor may include one light source, such as a single light emissive diode. In some implementations, a blood flow sensor may include more than one light sensor. For instance, a single light source may emit light that includes two wavelength ranges of interest, and two light sensors may be configured to selectively detect light at each of the two wavelengths (e.g., using suitable filters). The differential intensities measured with the two different light sensors (and thus different wavelength ranges) can then be used to analyze differential transmission/reflection by various features within the body tissue, such as arterial blood. Other examples are also possible. For instance, some examples may include one light sensor and one light source.

Other arrangements of the wearable device are also possible. For instance, light sources can also be situated to transmit light through body tissue toward a light sensor. In such an example, the light sensor can detect a signature of the amount of light transmitted through the body tissue rather than the amount reflected. In some cases, transmission-based arrangements may be suitable for being mounted at an extremity of a wearer, such as an end of a finger or toe, and reflection-based arrangements may be suitable for being mounted elsewhere.

IV. Environment Sensing From Ambient Light

Figure 4:
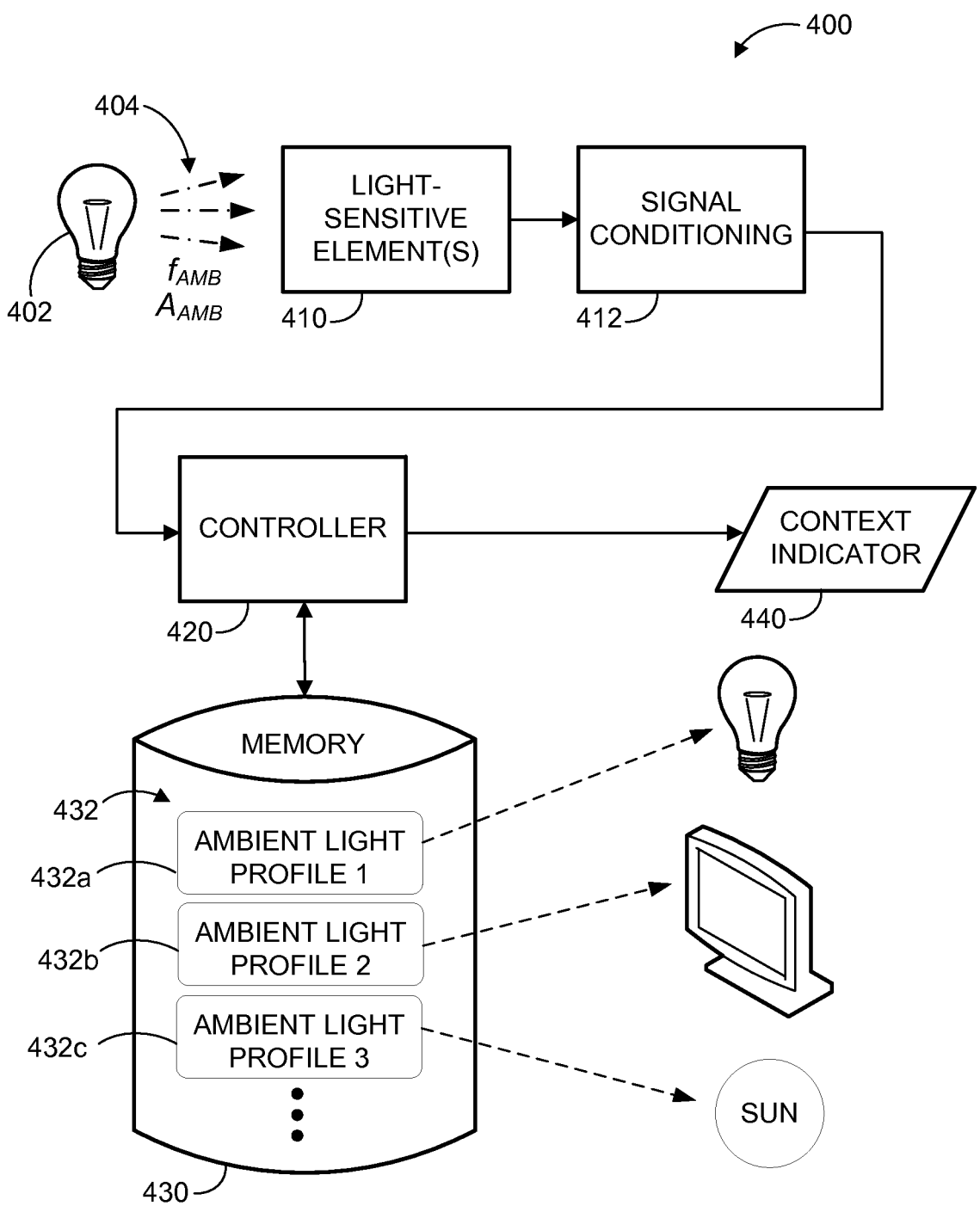
FIG. 4 is a simplified block diagram of an example system that can discriminate amongst environments based on characteristics of ambient light.

FIG. 4 is a simplified block diagram of a system 400 that can discriminate amongst environments based on characteristics of ambient light. The system 400 includes a light-sensitive element 410, a controller 420, and memory 430. The system 400 can function to obtain a set of measurements indicative of the intensity of incident light, analyze those measurements, determine a particular ambient light profile that corresponds to the set of measurements, and output an indication 440 of the determined profile. The light-sensitive element 410 used to obtain ambient light measurements may be combined with another system that obtains ambient light measurements for another purpose. In some examples, the system 400 may be implemented in combination with an optical blood sensor mounted on a wearable device, and that uses ambient light measurements to account for the effect of ambient light, similar to the wearable devices described above in connection with FIGS. 1-3. In some examples, the system 400 may be implemented in combination with an image capture system that includes an ambient light sensor to auto calibrate an exposure setting. In some examples, the system 400 may be implemented entirely independent of any other ambient light sensor systems.

The light-sensitive element 410 can function to generate an output signal indicative of an intensity of light incident on a light-sensitive area of the light-sensitive element 410. For example, the light-sensitive element 410 may be a photodiode that is reverse biased to generate a photocurrent based on the intensity of incident light via the photoelectric effect. While particular implementations may vary, a variety of signal conditioning electronics 412 can be used to convert the output signal generated by the light-sensitive element 410 to a digital value that can be analyzed by the controller 420. The signal conditioning electronics 412 may include a combination of amplifiers, filters, analog to digital converters, etc. For example, in an example in which the light-sensitive element 410 is a photodiode, the photocurrent from the photodiode can be used to charge or discharge a capacitive element during an integration time and the voltage of the capacitive element can be sampled to provide an indication of the light intensity. The sampled voltage can then be converted to a digital value using an analog to digital converter and the digital value can be communicated to the controller 420 for analysis.

The controller 420 can include a special purpose processor, such as a digital signal processor or a microprocessor that executes program logic (e.g., instructions stored in memory 430) to analyze a set of ambient light measurements. In some examples, the controller 420 may function to identify a frequency and/or amplitude of intensity modulations. The controller 420 may also include special purpose hardware modules that are configured to determine characteristics from a set of ambient light measurements, such as a frequency and/or amplitude of intensity modulations. The memory 430 can be a non-transient data storage that stores indications of a number of ambient light profiles 432. The controller 420 may refer to the memory 430 and determine whether a given set of ambient light measurements corresponds to any of the ambient light profiles 432. For instance, the controller 430 may determine that a frequency and/or amplitude of intensity modulations correspond to one of the ambient light profiles 432a, 432b, 432c.

As an example, the first ambient light profile 432a may characterize artificial lighting powered by an AC power supply (e.g., data indicative of light intensity modulated at 120 Hz); the second ambient light profile 432b may characterize lighting from a computer monitor (e.g., data indicative of light intensity modulated at a refresh rate of a computer monitor); and the third ambient light profile 432c may characterize solar lighting (e.g., data indicative of light intensity that is not modulated). For example, as shown in FIG. 4, the ambient light 404 emitted from the artificial light source 402 can be intensity modulated with a characteristic frequency $f_{AMB}$ and a characteristic amplitude $A_{AMB}$ (e.g., a frequency of about 120 Hz due to a 60 Hz AC power supply). Depending on the sampling frequency of the ambient light measurements, the intensity modulation frequency $f_{AMB}$ of the ambient light 404 may or may not be unambiguously determinable. For instance, if the sampling frequency is less than the twice $f_{AMB}$, the set of ambient light measurements may exhibit an intensity modulation that is a mixing frequency between the sampling frequency and $f_{AMB}$. Thus, some embodiments of the present disclosure include undersampling an intensity modulation frequency of ambient light and determining that the set of ambient light signals correspond to the undersampled intensity modulation frequency based on the measurements exhibiting an intensity modulation at a mixing frequency.

Additionally or alternatively, the controller 420 may determine extents of correlations between a given set of ambient light measurements and one or more of the ambient light profiles 432. For example, the controller 420 may determine a best fit correlation between the set of ambient light measurements and a function (or sample data set) indicative of the first ambient light profile 432a. The determined extents of correlation between the set of ambient light measurements and each of the ambient light profiles 432 can then be used to determine which, if any, of the ambient light profiles 432 the set of ambient light measurements corresponds to. In some examples, the determination that the set of ambient light measurements corresponds to the first ambient light profiles 432a may involve comparing a determined extent of correlation for the first ambient light profile 432a with a threshold value and/or with determined extents of correlation for one or more other ambient light profiles.

Upon determining that a set of ambient light measurements corresponds to one of the ambient light profiles 432, the controller 420 can output a context indicator 440, which may indicate which of the ambient light profiles 432 the set of measurements was determined to correspond to. The context indicator 440 may then be stored in a non-transient data storage (e.g., the memory 430), and may be used for a variety of purposes. For example, the context indicator 440 may be used to inform a context-sensitive setting of one or more user interfaces associated with the system 400 to be adjusted. For instance, the system 400 may be incorporated in a electronic device with a user interface setting, such as a cell phone, head-mountable device, laptop, etc., and the environmental context information provided by the context indicator 440 may be used to change a volume setting, an alert setting, a ring setting, etc., on the device.

Moreover, the system 400 may be incorporated in a wearable device associated with a particular wearer (e.g., a wristband), and may communicate with one or more other electronic devices also associated with the wearer (e.g., cell phone, head-mountable device, wrist-mounted device, etc.) so as to cause those devices to modify a user interface setting based on the context indicator 440. For instance, the system 400 may function to determine that a set of ambient light measurements correspond to an indoor environment (e.g., based on a correspondence with the first ambient light profile 432*a*), and the context indicator 440 can be sent to one or more devices that then adjust settings to an indoor mode of operation (e.g., vibration ring tone, reduced display emissivity, etc.). Many other examples are also possible.

Additionally or alternatively, the context indicator 440 may be tracked over time to provide an indication of the environments in which the system 400 has operated. Such historical environmental/context information may then be used to perform personalized analytics for the wearer, such as indications of their average amount of time indoors/outdoors or in the presence of a computer monitor. Such an analytics system may then help the wearer to reach target goals for outdoor recreation time, work hours, and/or some other factor related to context indicated by ambient light measurements by providing personalized analytics reports to the wearer.

Moreover, in some examples, the context indicator 440 may be used in combination with other factors to determine that a wearer is in a given environment and/or context. For example, an environmental context decision engine may receive information from a calendar and/or scheduling system associated with the wearer, information from other real time sensors, such as microphones, cameras, inertial sensors, etc., and/or information from real time user inputs from the wearer. In some cases, a wearer may provide an indication of a current environment, which may be used to supplement and/or correct context determinations and/or to help calibrate the ambient light profiles 432.

Figure 5:
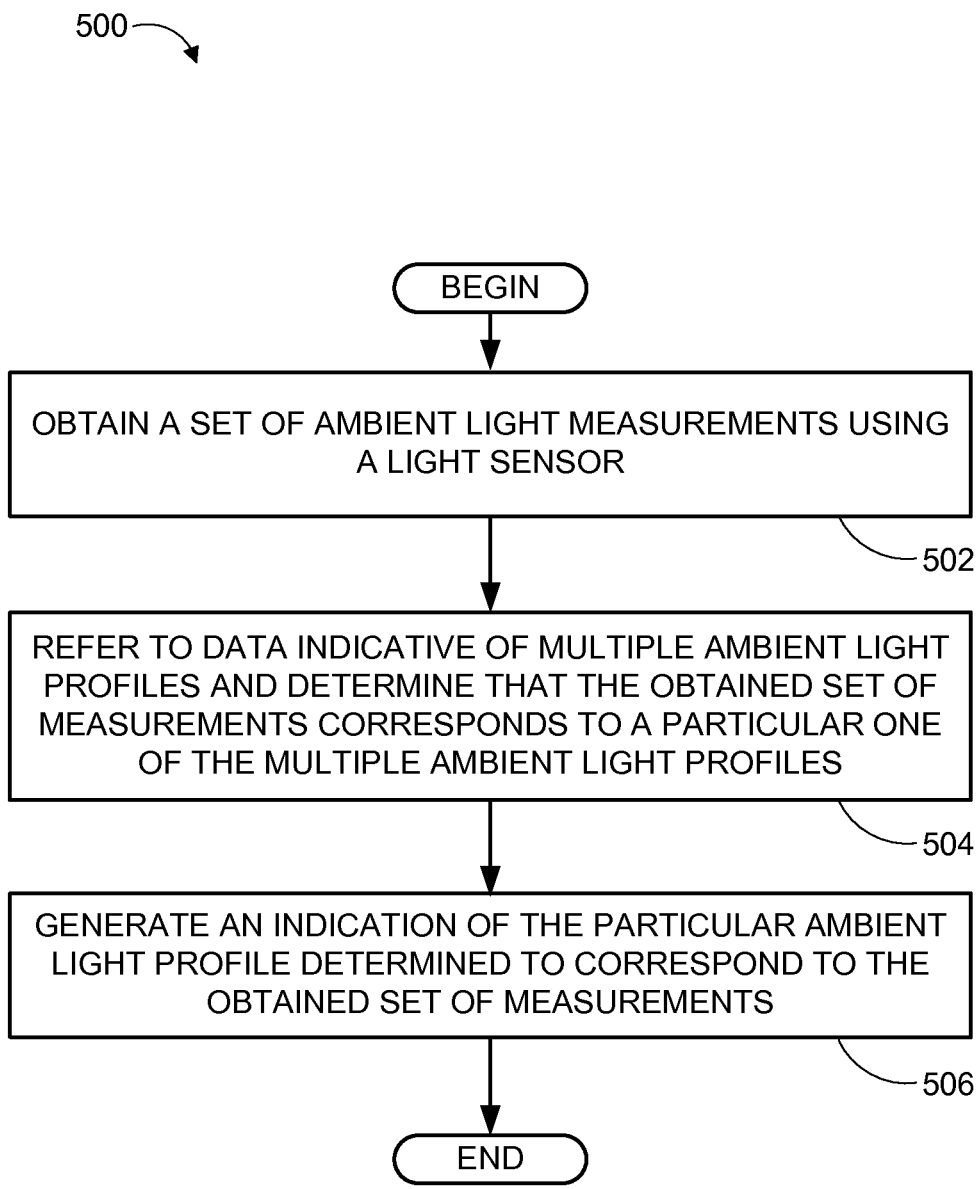
FIG. 5 is a flow chart of an example process.

FIG. 5 is a flow chart of an example process 500. The example process 500 may be performed by the system 400, for example. At block 502, a set of ambient light measurements are obtained using a light-sensitive element. The light-sensitive element may be configured to generate an output signal indicative of an intensity of light incident on the light-sensitive element. For example, a photodiode may be configured to generate a photocurrent related to the intensity of incident light. The output values from the light-sensitive element can then be converted to digital values (e.g., via an analog to digital converter, signal conditioning and/or sampling electronics). Thus, the set of ambient light measurements can be a set of data values indicative of ambient light intensities incident on the light-sensitive element during respective integration times. For example, the set of ambient light measurements may be obtained from an optical blood flow sensor that interleaves ambient light measurements with arterial blood transmission/reflection measurements. The set of ambient light measurements may be obtained at regular intervals with a similar integration time to thereby facilitate comparisons between the measurements and identification of patterns within the set of ambient light measurements, such as a frequency and/or amplitude of intensity modulation.

In some examples, the process may also include obtaining a set of active light measurements indicative of light transmitted and/or reflected by body tissue. For example, a light source may be situated to emit light toward body tissue for transmission or reflection thereby, and the light-sensitive element may be situated to receive at least some of the emitted light that is transmitted and/or reflected by the body tissue to the light-sensitive element. Thus, each of the obtained active light measurements may be indicative of light incident on the light-sensitive element while the light source emits light toward the body tissue for transmission or reflection thereby. By contrast, each of the obtained ambient light measurements may be indicative of light incident on the light-sensitive element (e.g., the output signal generated by the light-sensitive element) while the light source is off. Moreover, in such an example, the process may further include determining a pulse rate of blood through the body tissue based on the obtained active light measurements (e.g., based on intensity modulation in the set of active light measurements due to pulsing blood flow within the body tissue). In addition, the determination of the pulse rate may involve accounting for ambient light based at least partially on one or more ambient light measurements in the obtained set of ambient light measurements.

At block 504, the process 500 involves referring to data indicative of multiple ambient light profiles and determining that the obtained set of measurements corresponds to a particular one of the multiple ambient light profiles. The determination may involve, for example, determining an extent of correspondence between each of the ambient light profiles and the obtained set of ambient light measurements, and then comparing those extents of correspondence amongst one another and/or a threshold value. The determination may involve, determining a frequency and/or amplitude of intensity modulations in the ambient light based on the set of ambient light measurements. The frequency and/or amplitude may then be compared with data indicating frequency and/or amplitudes (or ranges) associated with each of the ambient light profiles. The particular ambient light profile that corresponds with the set of ambient light measurements can then be determined.

In some examples, data indicative of the multiple ambient light profiles may be stored in a memory. The stored data may characterize each of the multiple ambient light profiles. Such information may include, for example, information indicative of an intensity modulation frequency and/or an intensity modulation amplitude. As used herein, intensity modulation frequency and intensity modulation amplitude refer to a frequency and an amplitude of intensity modulations, respectively. The determination at block 504 may include determining an ambient light intensity modulation frequency and selecting one of the ambient light profiles based at least partially on a correspondence between the determined ambient light modulation frequency and intensity modulation frequency information associated with the selected one of the ambient light profiles. Additionally or alternatively, the determination at block 504 may include determining an ambient light intensity modulation amplitude and selecting one of the ambient light profiles based at least partially on a correspondence between the determined ambient light modulation amplitude and intensity modulation amplitude information associated with the selected one of the ambient light profiles.

At block 506, the process 500 involves generating an indication of the particular ambient light profile that was determined to correspond to the obtained set of measurements. The indication may be saved in a memory, and may be used as a basis to modify one or more user interface settings and/or to provide analytics related to a wearer's environment. Further, a subsequent set of ambient light measurements may be obtained and the second set of ambient light measurements may be determined to correspond to a second one of the ambient light profiles. In some examples, a wearable device may repeatedly (e.g., continuously, periodically, intermittently) determine an ambient light profile that corresponds to a most recently obtained set of ambient light measurements. The wearable device may then generate indications corresponding to each determination, and the set of indications can be stored for future look-up, and/or for use in providing analytics related to the wearer's lifestyle and/or health state.

V. Example Wearable Sensor Device

Figure 6:
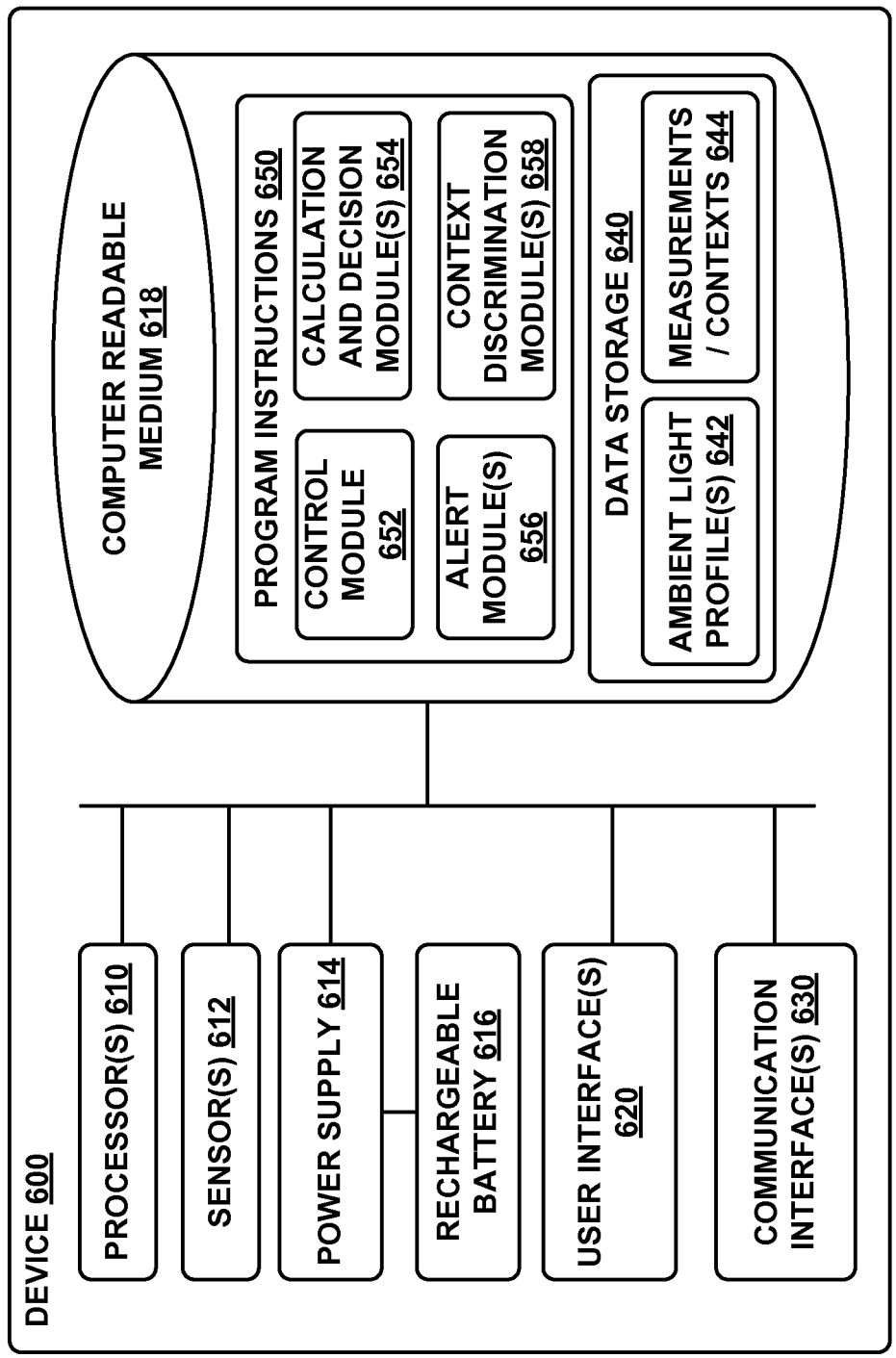
FIG. 6 is a functional block diagram of an example wearable device.

FIG. 6 is a functional block diagram of an example wearable device 600. The Device 600 may take the form of or be similar to one of the wearable devices and/or systems shown in FIGS. 1-4. However, device 600 may also take other forms, such as an ankle, waist, or chest-mounted device. Device 600 could also take the form of a device that is not configured to be mounted to a body. For example, device 600 could take the form of a handheld device configured to be maintained in proximity to an environment of interest (e.g., a body part, a biological sample container, a volume of a water treatment system) by a user or operator of the device 600 or by a frame or other supporting structure. Device 600 also could take other forms.

In particular, FIG. 6 shows an example of a device 600 having a processor 610, a sensor 612, a power supply 614, a rechargeable battery 616, a computer readable medium 618, a user interface 620, and a communication interface 630 for transmitting data to a remote system. The components of the device 600 may be disposed on a mount or on some other structure for mounting the device to enable stable detection of one or more properties of an environment of interest (e.g., of a body of a wearer of the device 600), for example, to an external body surface where a portion of subsurface vasculature or other physiological feature is observable.

Processor 610 may be a general-purpose processor or a special purpose processor (e.g., digital signal processors, application specific integrated circuits, etc.). The one or more processors 610 can be configured to execute computer-readable program instructions 650 that are stored in the computer readable medium 618 and that are executable to provide the functionality of device 600 described herein.

The computer readable medium 618 may include or take the form of one or more non-transitory, computer-readable storage media that can be read or accessed by at least one processor 610. The one or more computer-readable storage media can include volatile and/or non-volatile storage components, such as optical, magnetic, organic or other memory or disc storage, which can be integrated in whole or in part with at least one of the one or more processors 610. In some embodiments, the computer readable medium 618 can be implemented using a single physical device (e.g., one optical, magnetic, organic or other memory or disc storage unit), while in other embodiments, the computer readable medium 618 can be implemented using two or more physical devices.

A. Sensor(s)

Sensor 612 could include a component configured to detect one or more properties of an environment proximate to the sensor 612 (e.g., skin of an external body surface of a wearer of the device 600) and/or of energy or matter received from the proximate environment. As described above, the sensor 612 may include any component or components capable of detecting at least one property, which could include any properties that may relate to the environment being analyzed by the device (e.g., the body of the wearer or a subsection thereof). For example, the sensor 612 could be configured to measure blood pressure, pulse rate, blood oxygenation, ambient light intensity, skin temperature, etc. In some examples, the sensor 612 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. In examples wherein the sensor 612 includes a light sensor, the light sensor could be a photodiode, a photomultiplier, a CCD, a photocell, a photoresistive element, a camera, or any other sensor or sensors configured to detect one or more properties of light emitted by color centers of the functionalized nanodiamonds.

The sensor 612 could additionally include a light source or other energy emitter for transmitting illumination or other energy that can illuminate and/or penetrate the environment to illuminate, excite, or otherwise affect one or more elements of interest in the environment proximate to the sensor 612 (e.g., a fluorescent contrast agent configured to bind to an analyte of interest in blood of a wearer of the device 600). The wavelength of transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission of light by fluorophores, chromophores, or other elements of interest. An energy emitter of the sensor 612 could be configured to produce other forms of energy toward the environment proximate to the sensor 612 that could result in emission, reflection, scattering or some other generation of light or other energy or matter by other chemicals, imaging agents, biological elements, or other analytes proximate to the sensor 612.

B. Power Supply

The power supply 614 may include a coil configured to receive electromagnetic energy. The coil can be shaped such that the windings of the coil enclose a region of the device 600 wherein the sensor 612 is disposed (e.g., a perimeter of the sensor housing). The coil can be configured in a number of ways to enable efficient reception of electromagnetic energy using the coil or to enable and/or facilitate a number of other applications. The windings of the coil could be disposed proximate to a peripheral portion of a skin-contact surface of the sensor housing such that an area enclosed by the coil (e.g., a central portion of the contact surface of the housing) is maximized and/or such that a separation distance between the coil and a charging coil of a wireless charger is minimized. The windings of the coil may be arranged as a perimeter of any closed shape, such as a rectangular shape, an elliptical shape, or some other shape according to an application; for example, the shape of the coil could correspond to the shape of the contact surface of the housing of the device 600. The coil, and/or other components could be configured to enable efficient reception of electromagnetic energy of a specific frequency (e.g., 100 kilohertz to 200 kilohertz) by the coil. For example, the coil and a capacitor coupled to the coil could be configured to have a resonant frequency equal to the specific frequency of the electromagnetic energy. In some examples, the power supply 614 may include one or more other energy harvesting and/or energy receiving devices, such as a photovoltaic cell, or an electrical terminal for plugging in to a DC power source (e.g., to recharge the rechargeable battery 616).

Rechargeable battery 616 is configured to power the device 600 using stored electrochemical energy and to be recharged multiple times. The rechargeable battery 616 could include one or more of a variety of rechargeable battery chemistries, including lead-acid, nickel-metal-hydride, nickel-cadmium, lithium-ion, lithium-polymer, or some other rechargeable battery chemistry. Power supply 614 is configured to recharge the rechargeable battery 616 by applying a constant current, a constant voltage, a trickle current, or some other electrical energy having one or more specified properties to two or more electrodes of the rechargeable battery 616. The rechargeable battery 616 could include one or more thermistors that the processor(s) 610, the power supply 614, or some other component of the device 600 could operate to determine a temperature of the rechargeable battery 616 and to prevent damage of the rechargeable battery 616 by reducing a charging rate, a discharging rate, or some other property of use of the rechargeable battery 616 to prevent damage of the rechargeable battery 616.

The power supply 614 is configured to provide power to the device 600 from the rechargeable battery 616 and to recharge the rechargeable battery 616 using electromagnetic energy received using a coil or another energy receiving system. In examples including an energy harvesting coil, the power supply 614 could include components configured to facilitate the reception of electromagnetic energy by the coil. For example, the power supply 614 could include a fixed and/or variable capacitor configured to act as part of an LC tank circuit with the coil such that the LC tank circuit had a resonant frequency substantially equal to a frequency of electromagnetic energy directed toward the coil. In some examples, the power supply 614 could be configured to load the coil or otherwise alter one or more properties of the coil and/or power supply 614 in order to use the coil to communicate with an external system. For example, the power supply 614 could alter a load presented to the coil such that the coil could reflect backscatter electromagnetic radiation toward a wireless charger in order to communicate a charge state, a required power level, or some other property of the coil and/or device 600. Thus, in some examples, an energy harvesting coil may also be used to wirelessly communicate information from the device 600.

C. Example Device Functionality

The program instructions 650 stored on the computer readable medium 618 may include instructions to perform any of the methods described herein. For instance, in the illustrated embodiment, program instructions 650 include a controller module 652, calculation and decision module 654, an alert module 656, and a context discrimination module 658.

The controller module 652 can include instructions for operating the sensor 612. For example, the controller 652 may operate a light source and/or light sensors of the sensor 612 during each of a set of pre-set measurement periods. The controller module 652 can include instructions for operating the power supply 614 to recharge the rechargeable battery 616. The controller module 652 can also include instructions for operating the user interface 620. For example, controller module 652 may include instructions for operating the user interface 620 to convey alerts or other information to the wearer of device 600 via user interface 620. Further, controller module 652 may include instructions to execute certain functions based on inputs accepted by the user interface 620, such as inputs accepted by one or more buttons disposed on the user interface.

Communication platform 630 may also be operated by instructions within the controller module 652, such as instructions for sending and/or receiving information via a wireless antenna, which may be disposed on or in the device 600. The communication interface 630 can optionally include one or more oscillators, mixers, frequency injectors, etc. to modulate and/or demodulate information on a carrier frequency to be transmitted and/or received by the antenna. In some examples, the device 600 is configured to indicate an output from the processor 610 by modulating an impedance of the antenna in a manner that is perceivable by a remote server or other remote computing device.

Calculation and decision module 654 may include instructions for receiving data from the sensor 612, analyzing the data to determine one or more properties of an environment proximate to the sensor 612 (e.g., of a body of a wearer of the device 600), such as concentration of a target analyte, analyzing the data to determine if a medical condition or other specified condition is indicated, or other analytical processes relating to the environment proximate to the device 600. In particular, the calculation and decision module 654 may include instructions for determining, for each preset measurement time, the presence, concentration, and/or other properties of a clinically-relevant analyte based on the one or more properties of light emitted by contrast agents in a lumen of subsurface vasculature of a user of the device 600; and determining whether a medical condition is indicated based on at least the corresponding presence, concentration, or other property of the clinically-relevant analyte. These instructions could be executed at each of a set of preset measurement times (e.g., to obtain a set of measurements at a periodic interval).

The program instructions of the calculation and decision module 654 may, in some examples, be stored in a computer-readable medium and executed by a processor located external to the device 600. For example, the device 600 could be configured to collect certain data regarding physiological parameters from the user and then transmit the data to a remote server, which may include a mobile device, a personal computer, a network-connected server, the cloud, or any other remote system, for further processing.

The computer readable medium 618 may further contain other data or information (e.g., in data storage 640), such as medical and health history of a user of the device 600. The additional information may be useful in determining whether a medical condition or some other specified condition is indicated by sensor measurements. Further, the computer readable medium 618 may contain data corresponding to certain physiological parameter baselines, above or below which a medical condition is indicated. The baselines may be pre-stored on the computer readable medium 618, may be transmitted from a remote source, such as a remote server, or may be generated by the calculation and decision module 654. For example, the calculation and decision module 654 may include instructions for generating individual baselines for the user of the device 600 based on data collected over a certain number of measurement periods. For example, the calculation and decision module 654 may generate a baseline concentration of a pulse rate and galvanic skin resistance for each of a plurality of measurement periods by averaging the pulse rate and galvanic skin resistance at each of the measurement periods measured over the course of a few days, and store those baseline pulse rates and galvanic skin resistances in the computer readable medium 618 for later comparison. Baselines may also be generated by a remote server and transmitted to the device 600 via communication interface 630.

The calculation and decision module 654 may also, upon determining that a medical or other emergency condition is indicated, generate one or more recommendations for the user of the device 600 based, at least in part, on consultation of a clinical protocol. Such recommendations may alternatively be generated by the remote server and transmitted to the device 600 or to another device associated with the user. In some cases, an alert module 656 may be used to generate alerts or other information that is provided to the wearer based in part on outcomes from the calculation and decision module 654.

In some examples, the collected physiological parameter data, baseline profiles, health state information input by device users, generated recommendations, and/or clinical protocols may additionally be communicated to a cloud network and made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 654 that a medical or other specified condition is indicated, the alert module 656 may generate an alert and communicate information indicated by the alert via the user interface 620. The generated alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

In addition, the program instructions 650 can include a context discrimination module 658 that causes the device 600 to determine an environmental surrounding and/or context of the device 600 based on analysis of sensor data. For example, the context discrimination module 600 may include instructions that cause the device 600 to obtain a set of ambient light measurements (e.g., via the sensor(s) 612), analyze those measurements and determine that the set of measurements corresponds to a particular one of multiple ambient light profiles, and generate an indication of the particular ambient light profile. The context discrimination module 600 may include program instructions that cause the device 600 to function the same or similarly to the wearable device described in connection with FIGS. 4-5. Accordingly, in some examples, the context discrimination module 658 may include program instructions for performing signal processing analyses on a set of ambient light measurements, such as instructions for identifying a frequency and/or amplitude of intensity modulation based on the set of measurements. The context discrimination module 658 may also include program instructions for selecting one of multiple ambient light profiles that corresponds to a given set of ambient light measurements. Such selection may involve comparison(s) with threshold value(s) and/or comparisons amongst multiple extents of correspondence determine for respective ambient light profiles.

The context discrimination module 658 may also refer to data indicative of multiple ambient light profiles 642 stored in data storage 640, and use that data to determine that given set of ambient light measurements corresponds to one of the ambient light profiles 642. The data indicative of the ambient light profiles 642 may include, for example, values and/or ranges indicating characteristic frequency and/or amplitude of intensity modulation for each of the ambient light profiles. Upon determining that a given set of ambient light measurements corresponds to a particular ambient light profile, the context discrimination module 658 may also store data indicative of that determination in the data storage 640 as context data 644. The context data 644 can include information indicative of a set of ambient light measurements and/or information indicative of a determined ambient light profile that corresponds to a set of ambient light measurements. The context data 644 can also include an indication of a time and/or location of the device 600 (e.g., as indicated by sensor(s) 612) to facilitate analytics performed using the archived context data 644.

D. System with Multiple Wearable Devices

Figure 7:
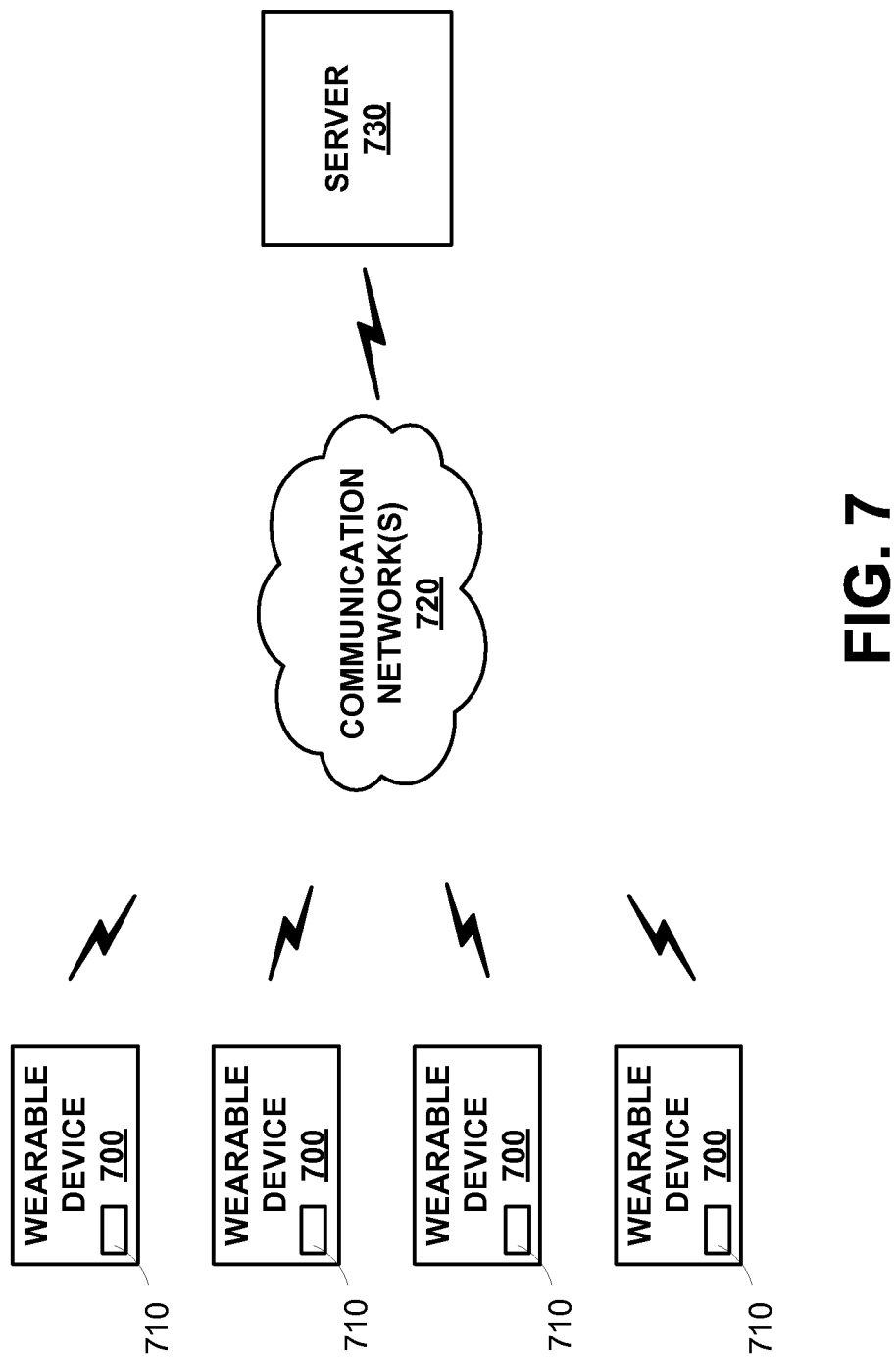
FIG. 7 is a functional block diagram of wearable devices communicatively linked via a network, according to an example embodiment.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user and/or one or more properties of a wearer detected using a sensor disposed in the wearable device 700, the server 730 may also be configured to gather and/or receive either from the wearable device 700 or from some other source, information regarding a wearer's overall medical history, environmental factors (e.g., ambient lighting profile), and/or geographical data. For example, a user account may be established on the server 730 for every wearer that includes information indicative of the wearer's medical history (or a portion thereof). Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server 730 may be configured to receive data regarding a wearer's health state from a hospital or physician. Such information may be used in the server's decision-making process, such as recognizing correlations and in generating clinical protocols.

Additionally, the server 730 may be configured to gather and/or receive the date, time of day, geographical location, and/or ambient environment information for each wearer of the wearable device(s) 700 during each measurement period. Such information may be used to detect and monitor spatial and temporal spreading of diseases and/or conditions in which health conditions manifest. As such, the wearable device 700 may be configured to determine and/or provide an indication of its own location and/or environment. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible. Moreover, the wearable device 700 and/or server 730 may be configured to determine its environmental context (e.g., indoors, outdoors, aboard an aircraft, in the presence of a computer monitor, etc.) based on a set of ambient light measurements (e.g., by comparing the set of ambient light measurements with multiple ambient light profiles and determining that one of the ambient light profiles corresponds to the set of measurements).

The server 730 may also be configured to make determinations regarding the efficacy of a drug or other treatment based on information regarding the drugs or other treatments received by a wearer of the device and, at least in part, the physiological parameter data and the indicated health state of the user. From this information, the server 730 may be configured to derive an indication of the effectiveness of the drug or treatment. For example, if a drug is intended to treat nausea and the wearer of the device does not indicate that he or she is experiencing nausea after beginning a course of treatment with the drug, the server 730 may be configured to derive an indication that the drug is effective for that wearer. In another example, a wearable device may be configured to measure blood glucose. If a wearer is prescribed a drug intended to treat diabetes, but the server 730 receives data from the wearable device indicating that the wearer's blood glucose has been increasing over a certain number of measurement periods, the server 730 may be configured to derive an indication that the drug is not effective for its intended purpose for this wearer. The server 730 may then cause information based on such determinations to be communicated to the wearer of the device 700. The server 730 could send a communication to the wearable device 700, which can provide information to the wearer via a user interface of the wearable device 700, or the server 730 could send such a communication to another device associated with the wearer (e.g., an email or text message) and/or to the wearer's health provider or guardian.

Further, some embodiments of the system may include privacy controls which may be automatically implemented or controlled by the wearer of the device 700. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of the device 700 may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

VI. Alternative Embodiments

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in which embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
an active light source that emits light toward a body tissue of a wearer of the system;
a light-sensitive element, wherein at least some of the emitted light from the active light source is transmitted or reflected by the body tissue and incident on the light-sensitive element, and wherein the light-sensitive element generates an output signal indicative an intensity of the light from the active light source that is incident on the light-sensitive element and an intensity of light from an ambient light source that is incident on the light-sensitive element;
a processor; and
a computer readable medium storing program instructions, wherein the program instructions are executable by the processor to perform operations comprising: (i) obtaining a set of active light measurements using the light-sensitive element, wherein each of the active light measurements is indicative of light incident on the light-sensitive element while the active light source emits light toward the body tissue for transmission or reflection thereby; (ii) determining, based on the obtained active light measurements, a pulse rate of blood through the body tissue; (iii) obtaining a set of ambient light measurements using the light-sensitive element, wherein the set of ambient light measurements is sampled at a rate of less than twice an intensity-modulated characteristic frequency of the ambient light source and comprises data values indicative of ambient light intensities, and wherein each of the ambient light measurements in the set of ambient light measurements is based on an output signal from the light-sensitive element generated while the active light source is off; (iv) determining that the obtained set of ambient light measurements corresponds to a particular one of multiple ambient light profiles by at least determining an ambient light intensity modulation frequency based on the set of ambient light measurements and selecting the particular one of the multiple ambient light profiles based on a correspondence between the determined ambient light intensity modulation frequency and intensity modulation frequency information associated with the particular one of the multiple ambient light profiles, wherein the multiple ambient light profiles include at least a profile of artificial lighting powered by an alternating current (AC) power supply and a profile of solar lighting; and (v) in response to determining that the obtained set of ambient light measurements corresponds to the particular one of the multiple ambient light profiles, modifying a user interface setting of a device communicatively linked to the system.

2. The system of claim 1, wherein the computer readable medium further stores data indicative of the multiple ambient light profiles, wherein the stored data comprises information that characterizes each of the multiple ambient light profiles, and wherein the information that characterizes a given ambient light profile includes information indicative of an intensity modulation frequency for the given ambient light profile.

3. The system of claim 1, further comprising a housing comprising a body-mountable surface, and wherein the light-sensitive element is mounted to the housing.

4. The system of claim 3, wherein the light-sensitive element is situated such that, while the body-mountable surface is mounted over body tissue, at least a portion of light incident on the light-sensitive element passes through the body tissue.

5. The system of claim 1, wherein the operations further comprise, after obtaining the set of ambient light measurements: (i) obtaining a second set of ambient light measurements using the light-sensitive element; (ii) determining that the obtained second set of ambient light measurements corresponds to a second particular one of the multiple ambient light profiles; and (iii) in response to determining that the obtained second set of ambient light measurements corresponds to the second particular one of the multiple ambient light profiles, generating an indication that the obtained second set of ambient light measurements corresponds to the second particular one of the multiple ambient light profiles.

6. The system of claim 1, further comprising an analog to digital converter configured to generate data values based on output signals from the light-sensitive element.

7. The system of claim 1, wherein the multiple ambient light profiles further include a profile of lighting from a computer monitor.

8. The system of claim 1, further comprising determining an environment or context of the system based at least in part on the particular one of the multiple ambient light profiles.

9. The system of claim 8, wherein determining the environment or context of the system further comprises determining a time or location of the system.

10. The system of claim 8, wherein the operations further comprise reporting both the determined pulse rate of the wearer and the determined environment or context of the system to a server for tracking the determined environment or context of the system over time and identifying one or more behavioral patterns or health states of the wearer based on both the determined pulse rate of the wearer and the tracked environment or context of the system.

11. The system of claim 10, wherein the operations further comprise using the identified one or more behavioral patterns or health states of the wearer to evaluate an effectiveness of a drug or treatment.

12. The system of claim 10, wherein identifying one or more behavioral patterns or health states of the wearer based on both the determined pulse rate of the wearer and the tracked environment or context of the system comprises:
using the tracked environment or context of the system to determine an amount of time the wearer has spent indoors or outdoors.

13. The system of claim 10, wherein the operations further comprise using an input received from the wearer to identify the one or more behavioral patterns or health states of the wearer.

14. The system of claim 13, wherein the operations further comprise detecting or monitoring a spatial or temporal spreading of a disease based at least in part on the identified one or more behavioral patterns or health states of the wearer.

15. The system of claim 1, wherein modifying the user interface setting of the device communicatively linked to the system comprises modifying an audio setting of the device communicatively linked to the system.

16. The system of claim 1, wherein the device communicatively linked to the system is a cell phone, and wherein modifying the user interface setting of the device communicatively linked to the system comprises modifying a user interface setting of the cell phone.

17. The system of claim 1, wherein the operations further comprise using the obtained set of ambient light measurements for calibration of a pulse oximetry system.

18. The system of claim 1, wherein the operations further comprise receiving an indication of a current environment or context of the system and using the received indication to calibrate one or more of the ambient light profiles.

19. A method comprising:
using a light-sensitive element of a wearable device to obtain a set of active light measurements indicative of light transmitted or reflected by body tissue of a wearer of the wearable device, wherein each of the active light measurements is indicative of light incident on the light-sensitive element while an active light source emits light toward the body tissue for transmission or reflection thereby, and wherein the active light source is situated such that, while the active light source emits light toward the body tissue, at least some of the emitted light is transmitted or reflected by the body tissue to the light-sensitive element;
determining, based on the obtained active light measurements, a pulse rate of blood through the body tissue;
using the light-sensitive element to obtain a set of ambient light measurements indicative of an intensity of light from an ambient light source that is incident on the light-sensitive element, wherein the set of ambient light measurements is sampled at a rate of less than twice an intensity-modulated characteristic frequency of the ambient light source and comprises data values indicative of ambient light intensities, and wherein each of the ambient light measurements in the set of ambient light measurements is based on an output signal from the light-sensitive element generated while the active light source is off;
determining that the obtained set of ambient light measurements corresponds to a particular one of multiple ambient light profiles by at least determining an ambient light intensity modulation frequency based on the set of ambient light measurements and selecting the particular one of the multiple ambient light profiles based on a correspondence between the determined ambient light intensity modulation frequency and intensity modulation frequency information associated with the particular one of the multiple ambient light profiles, wherein the multiple ambient light profiles include at least a profile of artificial lighting powered by an alternating current (AC) power supply and a profile of solar lighting; and
in response to determining that the obtained set of ambient light measurements corresponds to the particular one of the multiple ambient light profiles, modifying a user interface setting of a device communicatively linked to the system.

20. The method of claim 19, further comprising:
storing data indicative of the multiple ambient light profiles, wherein the stored data comprises information that characterizes each of the multiple ambient light profiles, wherein the information that characterizes a given ambient light profile includes information indicative of an intensity modulation frequency for the given ambient light profile.

21. The method of claim 19, wherein determining the pulse rate comprises accounting for ambient light based on one or more ambient light measurements in the obtained set of ambient light measurements.

22. The method of claim 19, wherein obtaining the set of ambient light measurements comprises using an analog to digital converter to generate the data values based on output signals from the light-sensitive element.

23. The method of claim 19, further comprising, after obtaining the set of ambient light measurements:
obtaining a second set of ambient light measurements using the light-sensitive element;
determining that the obtained second set of ambient light measurements corresponds to a second particular one of the multiple ambient light profiles; and
in response to determining that the obtained second set of ambient light measurements corresponds to the second particular one of the multiple ambient light profiles, generating an indication that the obtained second set of ambient light measurements corresponds to the second particular one of the multiple ambient light profiles.

24. The method of claim 19, wherein the multiple ambient light profiles further include a profile of lighting from a computer monitor.

25. A body-mountable device comprising:
a housing comprising a body-mountable surface;
an active light source mounted to the housing, wherein, while the body-mountable surface is mounted over body tissue of a wearer, the active light source emits light toward the body tissue;
a light-sensitive element mounted to the housing, wherein at least some of the emitted light from the active light source is transmitted or reflected by the body tissue and incident on the light-sensitive element, and wherein the light-sensitive element generates an output signal indicative of an intensity of incident light from the active light source and an intensity of incident light from an ambient light source;
a processor; and
a computer readable medium storing program instructions, wherein the program instructions are executable by the processor to perform operations comprising: (i) obtaining a set of active light measurements using the light-sensitive element, wherein each of the active light measurements is indicative of light incident on the light-sensitive element while the active light source emits light toward the body tissue for transmission or reflection thereby; (ii) determining, based on the obtained active light measurements, a pulse rate of blood through the body tissue; (iii) obtaining a set of ambient light measurements using the light-sensitive element, wherein the set of ambient light measurements is sampled at a rate of less than twice an intensity-modulated characteristic frequency of the ambient light source and comprises data values indicative of ambient light intensities, and wherein each of the ambient light measurements in the set of ambient light measurements is based on an output signal from the light-sensitive element generated while the active light source is off; (iv) determining that the obtained set of ambient light measurements corresponds to a particular one of multiple ambient light profiles by at least determining an ambient light intensity modulation frequency based on the set of ambient light measurements and selecting the particular one of the multiple ambient light profiles based on a correspondence between the determined ambient light intensity modulation frequency and intensity modulation frequency information associated with the particular one of the multiple ambient light profiles, wherein the multiple ambient light profiles include at least a profile of artificial lighting powered by an alternating current (AC) power supply and a profile of solar lighting; (v) in response to determining that the obtained set of ambient light measurements corresponds to the particular one of the multiple ambient light profiles, modifying a user interface setting of a device communicatively linked to the system.

26. The body-mountable device of claim 25, wherein the computer readable medium further stores data indicative of the multiple ambient light profiles, wherein the stored data comprises information that characterizes each of the multiple ambient light profiles, and wherein the information that characterizes a given ambient light profile includes information indicative of an intensity modulation frequency for the given ambient light profile.

27. The body-mountable device of claim 25, wherein the multiple ambient light profiles further include a profile of lighting from a computer monitor.

* * * * *